US00PP08728P

United States Patent [19]

Schumann

[11] Patent Number: Plant 8,728

[45] Date of Patent: May 10, 1994

[54] GERANIUM PLANT NAMED FISTANTUT

[75] Inventor: Ingeborg Schumann, Albstadt, Fed. Rep. of Germany

[73] Assignee: Florfis AG, Binningen, Switzerland

[21] Appl. No.: 94,330

[22] Filed: Jul. 21, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Foley & Lardner

[57] ABSTRACT

A new and distinct cultivar of geranium named Fistantut, particularly characterized by the combined features of salmon pink and white semi-double flowers, almost ball shaped umbels, foliage with medium zonation, medium plant habit, and early spring flower response.

1 Drawing Sheet

The present invention comprises a new and distinct cultivar of geranium, botanically known as *Pelargonium zonale l'hert,* and hereinafter referred to by the cultivar name Fistantut.

Fistantut is a product of planned breeding program which had the objective of creating new geranium cultivars with light salmon pink flower color, medium growth habit, foliage with zonation, and good rooting and good branching ability.

Fistantut was originated from a hybridization made by inventor Ingeborg Schumann in a controlled breeding program in Galdar, Gran Canaria, Spain in 1986. The female parent was a hybrid produced by crossing the cultivars Tany and Achspen. Tany has salmon white semi-double flowers, and leaves with medium zonation. Achspen, disclosed in U.S. Plant Pat. No. 5,313 under the varietal name Lachsball, is characterized by light salmon semi-double flowers, compact plant habit, leaves without zonation, and early flower response. The male parent of Fistantut was Dresden Doll White, a cultivar having single white flowers, medium green foliage without zonation, and medium growth.

Fistantut was discovered and selected as one flowering plant within the progeny of the stated cross by Ingeborg Schumann in 1987 in a controlled environment in Galdar, Gran Canaria, Spain.

The fist act of asexual reproduction of Fistantut was accomplished when vegetative cuttings were taken from the initial selection in February 1989 in a controlled environment in Galdar, Gran Canaria, Spain, by, or under the supervision of, Ingeborg Schumann.

Horticultural examination of plants grown from these cuttings initiated in May 1989, and continuing thereafter, has demonstrated that the combination of characteristics as herein disclosed for Fistantut are firmly fixed and are retained through successive generations of asexual reproduction.

Fistantut has not been observed under all possible environmental conditions. The phenotype may vary significantly with variations in environment such as temperature, light intensity and day length without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristic of Fistantut, which in combination distinguish this geranium as a new and distinct cultivar:

1. Light salmon pink flower color
2. Semi-double flower form
3. Early to medium flower response
4. Ball shaped umbels of medium size
5. Comparatively good rain resistance
6. Medium green foliage with medium zonation
7. Medium plant habit Of the many commercial cultivars known to the present inventor, the most similar in comparison to Fistantut is Americana Light Salmon. Reference is made to attached Chart A which compares certain characteristics of Fistantut to those same characteristics of Americana Light Salmon. In general comparison to Americana Light Salmon, Fistantut has less intense, somewhat more pink and less salmon flower color, only medium growth habit, and weaker zonation on leaves.

The accompanying color photographic drawing shows typical flower and foliage characteristics of Fistantut, with colors being as true as possible with illustrations of this type.

In the following description color references are made to The Royal Horticultural Society Color Chart. The color values were determined indoors in May from plants grown indoors in Hillscheid, Federal Republic of Germany.

Classification:

*Botanical.*—A hybrid of the species *Pelargonium zonale l'Hert.*

*Commercial.*—Zonal geranium, cv., Fistantut.

INFLORESCENCE

A. Umbel:

*Shape.*—Almost spherical.

*Average diameter.*—95 mm.

*Average depth.*—78 mm.

*Peduncle length.*—160 mm.

*Peduncle color.*—Light green, 143 C.

*Pedicel length.*—27 mm.

*Pedicel color.*—Green, sometimes with a little anthocyanin.

*Number of flowers per umbel.*—60–80.

B. Corolla:

*Average diameter.*—45 mm.

*Form.*—Semi-double.

*Number of petals.*—8–14.
*Number of petaloids.*—0–1.
*Color (general tonality from a distance of three meters).*—Salmon pink.
*Color of petals.*—Upper surface, near center — Between 52 C/D and 55 C. Upper surface, near margin — White, about 56D.
*Color of lower surface.*—56 B-C.
*Color of sepals.*—Light Green.
*Number of sepals.*—5–6.

C. Bud:
*Shape.*—Round to elliptic.
*Color (adaxial).*—Light green.
*Color (abaxial).*—White to very light salmon.

D. Reproductive organs:
*Androecium.*—2–5 fertile anthers; white filaments and orange pollen.
*Gynoecium.*—5–6 lobes stigma, white style and pink stigma E. Spring flowering response period: In Hillscheid, Federal Republic of Germany, in 1993 plants had on average 1.1 flowers opened 10 weeks after planting of unrooted cuttings.

F. Outdoor flower production: The flower count in 1992 in Hillscheid, Federal Republic of Germany was between 30 and 35 flowers per plant for May through August observation period.

G. Durability: Shatter resistance good.

PLANT

A. Foliage:
*Form.*—Kidney-shaped.
*Margin.*—Bicrenated.
*Size of leaf.*—About 85 mm.
*Color of upper surface.*—Medium green, approximately 137D.
*Color of zonation.*—Brown, about 166A.
*Tolerance of botrytis.*—Average.

B. General appearance and form:
*Internode length.*—10–15 mm.
*Branching pattern.*—2.6 branches per week.
*Height (12 week old plants).*—14 cm.

CHART A

| CHARACTERISTICS | FISTANTUT | AMERICANA LIGHT SALMON |
|---|---|---|
| Flower color | 52 C-D | between 52 C and 44 D |
| Distinctness of zonation (ranging from 1 (very weak) to 9 (very strong) | 5, medium | 7, strong |
| Plant height | 14 cm | 18 cm |

I claim:

1. A new and distinct cultivar of geranium plant named Fistantut, as illustrated and described.

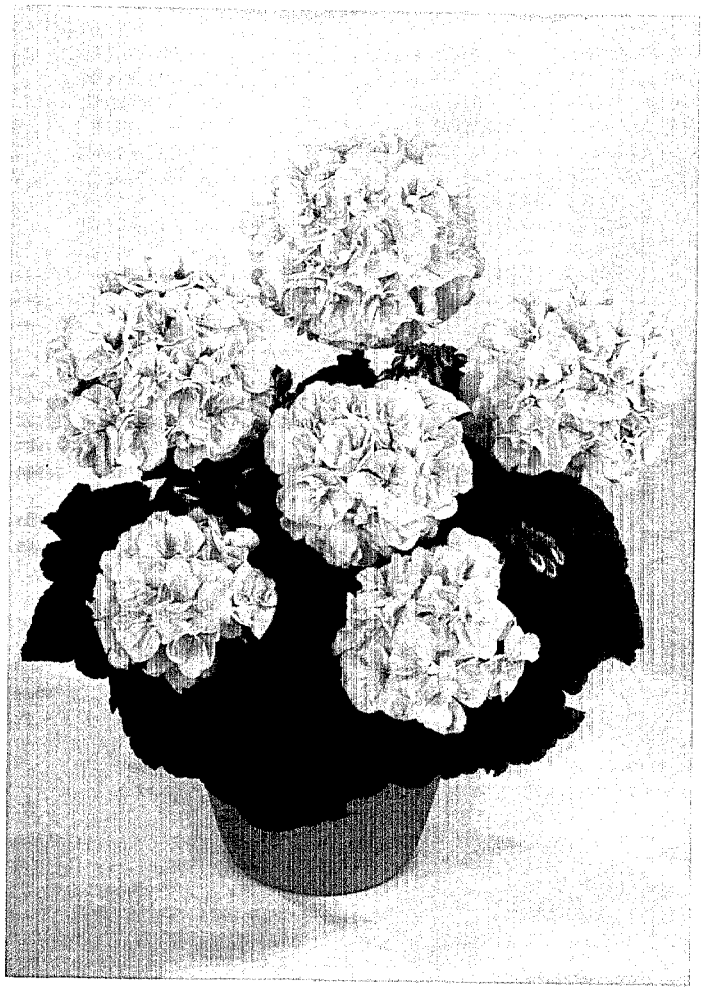

* * * * *